United States Patent [19]

Watson

[11] 4,208,349

[45] Jun. 17, 1980

[54] PROCESS FOR THE PREPARATION OF 2-[N-(2-HYDROXYETHYL)-N-LOWER ALKYLAMINOMETHYL]BENZHYDROLS

[75] Inventor: Peter G. Watson, Loughborough, England

[73] Assignee: Riker Laboratories, Inc., Northridge, Calif.

[21] Appl. No.: 17,589

[22] Filed: Mar. 5, 1979

Related U.S. Application Data

[63] Continuation of Ser. No. 928,600, Jul. 27, 1978.

[51] Int. Cl.$^2$ .............................................. C07C 85/12
[52] U.S. Cl. ........................... 260/570 R; 260/558 R; 260/559 D
[58] Field of Search ........ 260/570 R, 570 AB, 558 R, 260/558 D, 559 R

[56] References Cited

U.S. PATENT DOCUMENTS

| | | | |
|---|---|---|---|
| 3,830,803 | 8/1974 | Klohs et al. ..................... | 260/570 X |
| 3,978,085 | 8/1976 | Eberlin ................................. | 260/333 |
| 4,071,557 | 1/1978 | Mattner et al. ...................... | 260/570 |
| 4,083,871 | 4/1978 | Houlihan et al. ................... | 260/570 |

FOREIGN PATENT DOCUMENTS

| | | | |
|---|---|---|---|
| 863349 | 2/1971 | Canada ............................... | 260/510 R |
| 1148717 | 4/1969 | United Kingdom ................ | 260/570 R |

OTHER PUBLICATIONS

Ventron Alembic, "Reduction of Amides with Sodium Borohydride", pp. 6–7.

Umino et al., "Tetrahedron Letters", No. 10, pp. 763–766.

Maki et al., "Chemistry & Industry", Apr. 13, 1976, pp. 322–323.

*Primary Examiner*—Robert V. Hines
*Attorney, Agent, or Firm*—Cruzan Alexander; Donald M. Sell; Donald C. Gipple

[57] ABSTRACT

Process for the production of 2-[N-(2-hydroxyethyl)-N-lower alkylaminomethyl]benzhydrols by reducing N-(2-haloethyl)-N-lower alkyl-o-benzoylbenzamides in an inert solvent with sodium borohydride in the presence of an alkanoic acid.

11 Claims, No Drawings

PROCESS FOR THE PREPARATION OF 2-[N-(2-HYDROXYETHYL)-N-LOWER ALKYLAMINOMETHYL]BENZHYDROLS

This is a continuation of application Ser. No. 928,600 filed July 27, 1978.

The invention relates to a process for the production of 2-[N-(2-hydroxyethyl)-N-lower alkylaminomethyl]-benzhydrols (I). The benzhydrol products of this process can be converted directly to the corresponding phenylbenz(f)-2,5-oxazocines which are valuable physiologically active substances. Thus see Unites States Pat. No. 3,830,803, United States Pat. No. 3,978,085, British Pat. No. 1,148,717 and Canadian Patent 863,349.

The direct preparation of compounds of type I below from compounds of type II has been known heretofore. This known reaction is carried out by treatment of the starting compound with a metal hydride reducing agent, such as lithium aluminium hydride, in an inert organic solvent such as tetrahydrofuran or ether (e.g. see British Pat. No. 1,148,717). Reduction with lithium aluminium hydride is not, however, a practical synthetic method for large scale reactions on a commercial basis. The solvents which must be used are fire hazards, lithium aluminium hydride itself is extremely hazardous, and the costs are prohibitively high.

The present method, on the other hand, can be commercially feasible and advantageous. It uses less hazardous solvents, can be comparatively less expensive and can produce high yields of product of good purity.

This invention provides a process for the preparation of a 2[N-(2-hydroxyethyl)-N-lower alkylaminomethyl]-benzhydrol of the formula:

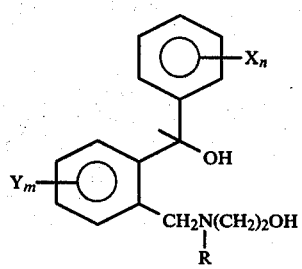

I wherein R is methyl or ethyl, X is fluorine, chorine, bromine or methyl, Y is fluorine, chlorine, methyl or methoxy, and m and n are independently zero, one or two which comprises reducing a compound of the formula

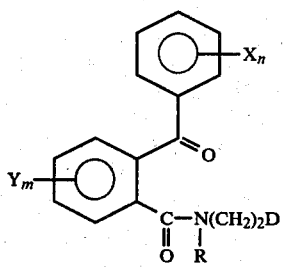

III where D is halogen in an inert solvent with sodium borohydride in the presence of an alkanoic acid. Preferably the compound of formula III is obtained by treating a compound of the formula

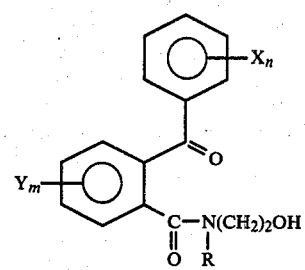

II with a halogenating agent in an inert solvent.

The reduction of certain amides to amines with sodium borohydride in the presence of alkanoic acid has been described in "Sodium Acyloxyborohydride as New Reducing Agents", Tetrahedron Letters No. 10, pages 763–766 and "Reduction of Amides with Sodium Borohydride", Ventron Alembic, Issue No. 9, pages 6 and 7, but this appears to be different from our reduction of the halogenated compound of formula III. Thus the prior described reductions require a large excess of sodium borohydride, with loss of efficiency due to evolution of $H_2$ and probable formation of amine-borane, the reduction allegedly proceeding by way of the alkyloxyborohydride. The reduction of the present invention, on the other hand, proceeds readily in a wide range of solvents with a much smaller excess of sodium borohydride; the presence of the halogen D is essential, the reaction failing in its absence, and in the preferred procedure, in which the formula III compound and alkanoic acid are added gradually to the reaction mixture containing all of the sodium borohydride, there is no evolution of $H_2$ after the first small acid addition.

The product I is ordinarily recovered from the reaction mixture by means of an aqueous workup in solution in the inert solvent. It can be obtained as a pure substance by removal of the solvent by conventional methods or the solution can be used as such, for example in preparing the physiologically active phenylbenz(f)-2,5-oxazocines.

The starting materials II of the process of the invention are generally known to the art (see the British and Canadian patents referred to hereinabove). The first (halogenation) step of the process is carried out in an inert solvent, such as a chlorinated hydrocarbon, for example dichloromethane or dichloroethane or an aromatic hydrocarbon such as toluene, benzene or the like. The preferred solvent is dichloroethane. Suitable halogenating agents include phosphorus trichloride, phosphorus tribromide, phosphorus pentachloride and thionyl chloride. Phosphorus trichloride is presently preferred due to its relatively low cost. Generally an equivalent amount or a small excess of up to about 10 percent of halogenating agent is used.

The temperature required is moderate, e.g. from 20° to 90° C., depending upon the time constraints. At 55° to 80° C., the reaction is complete in from about one to about four hours. Excessive reaction temperatures and reaction times should be avoided to minimize the possibility of side reactions. Completion of the reaction is generally monitored chromatographically. Preferably the reaction mixture is cooled, neturalized with aqueous base, then separated and dried.

The reduction reaction can be easily and economically carried out and produce high yields (e.g. from 80 to 100 percent of the theoretical amount). Unlike the prior art process which uses the powerful reducing agent lithium aluminium hydride and difficult and dangerous reaction conditions, the reduction step of the present process can be easily controlled even when carried out on a large scale.

The reaction is carried out in the presence of an alkanoic acid, preferably a lower alkenoic acid containing not more than four carbon atoms such as acetic acid. When the acid is omitted, little or none of the desired product is obtained. The amount of alkanoic acid used may for example be about 0.1 to about 1.0 mole per mole of sodium borohydride. The reduction is suitably carried out in an inert aliphatic chlorinated hydrocarbon solvent which has a reflux temperature in excess of 60° C., preferably dichloroethane. The reaction temperature is preferably the reflux temperature of the reaction mixture. It can be dangerous to start the reaction below a temperature of 60° C.

The reduction can be carried out by adding acetic acid to a mixture of sodium borohydride and the precursor N-(2-haloethyl)-N-lower alkyl-o-benzylbenzamide (III) in dichloroethane. This reaction is normally quite exothermic, although controllable. Alternatively (and preferably for large scale reactions) the reaction is begun on a relatively small scale with all reaction components being present. This initial reaction mixture, which includes the entire amount of sodium borohydride to be used in the larger scale reaction, is maintained at reflux. The balance of the precursor III in dichloroethane together with the alkanoic acid is added gradually. Using this alternate procedure, less alkanoic acid is necessary (for example less than 0.2 mole per mole of sodium borohydride). In addition, less sodium borohydride may also be used; for example, it is presently preferred to use about 1.5 moles per mole of III compared to 2.0 moles per mole of III when not using the preferred procedure. The reaction can be carried out under an inert (e.g. nitrogen) atmosphere as a safety measure and also to minimize the possibility of side reactions, although this is generally unnecessary.

After the reduction has proceeded to completion (as conveniently shown by chromatographic analysis), the mixture is added gradually (cautiously at first) to water, then basified and heated at reflux (to destroy any residual sodium borohydride and neutralize the alkanoic acid). The product can then be isolated or alternatively the organic layer containing the product can be separated and used for further reaction to provide the pharmaceutically active phenylbenz(f)-2,5-oxazocines.

The following illustrative Examples are provided to show the practice of the process of the invention. Example 2 illustrates just the preparation of a starting compound III.

EXAMPLE 1

A complete five-step synthetic sequence beginning with commercially available materials and ending with a pharmaceutically active phenylbenz(f)-2,5-oxazocine.

Steps 3 and 4 of this example illustrate a preferred process of the present invention as part of the sequence.

Step 1—Acid Chloride Preparation.

To a slurry of ortho-benzoylbenzoic acid (222.2 g., 1.0 mole) in dichloroethane (230 ml.) was added in one portion phosphorous trichloride (35.4 ml., 0.46 mole).

After one hour of stirring, the temperature had reached a maximum of 39° C. Stirring at room temperature was continued overnight after which thin layer chromatographic analysis showed complete conversion to the acid chloride. The product layer was separated by decantation.

Step 2—Amide Formation.

To a solution of triethylamine (111.39 g., 1.1 mole) and N-methyl ethanolamine (82.62 g., 1.1 mole) in dichloroethane (400 ml.) was added dropwise the acid chloride-dichloroethane solution of step 1 over one hour at 5° to 12° C. After the addition was complete, the reaction mixture was stirred for an additional hour, by which time thin layer chromatographic analysis showed complete conversion to N-(2-hydroxyethyl)-N-methyl-o-benzoylbenzamide.

Step 3—Preparation of N-(2-chloroethyl)-N-methyl-o-benzoylbenzamide

To a slurry of product obtained in step 2 at room temperature was added phosphorus trichloride (35.4 ml., 0.406 mole) over five minutes. This caused a 20° C. temperature rise, and the slurry thinned considerably. After warming to 55° to 60° C., and maintaining this temperature for one hour, thin layer chromatographic analysis showed complete conversion to the desired product. The reaction mixture was cooled to 0° C., and diluted with water (500 ml.) over five minutes maintaining the temperature below 5° C. The two-phase mixture was stirred for five minutes and the layers allowed to separate. The bottom organic layer was washed with an additional 500 ml. of water and sufficient base (sodium hydroxide) to raise the pH to about 7 at below 10° C., and the bottom layer was dried over anhydrous sodium sulfate (90 g.).

Step 4—Reduction.

To a slurry of a portion of the solution from step 3 (108 ml.) and sodium borohydride (28.4 g., 0.75 mole) was added dropwise acetic acid (3.5 ml.). After frothing and heat evolution had ceased, the temperature was raised to reflux and maintained for 15 minutes. To this refluxing slurry was added dropwise with stirring over two hours the remainder of the solution of product from step 3 containing 9 ml. of acetic acid. The temperature was maintained at reflux by slight warming of the flask, the addition itself being fairly exothermic. After the completion of addition, the reaction mixture was stirred at reflux for a further hour, at which time thin layer chromatographic analysis showed complete conversion to the desired product. The whole of this procedure was carried out under an atmosphere of nitrogen.

To the above slurry at room temperature was added dropwise over one hour (very slowly initially) 200 ml. of water. The addition caused fairly heavy effervescence, and the temperature rose to 45° C. To the above diluted reaction mixture was added 40 percent aqueous sodium hydroxide (75 ml.). The temperature was raised to reflux and maintained for three quarters of an hour. The mixture was then cooled and the layers separated to provide a solution of 2-[N-(2-hydroxyethyl)-N-methylaminomethyl]benzhydrol in dichloroethane.

Step 5—Cyclization.

The benzhydrol from step 4 (still in solution in dichloroethane) was cyclized with aqueous hydrobromic acid using the method of U.S. Pat. No. 3,978,085. The reaction yielded 131.5 g. of 5-methyl-1-phenyl-1,3,4,6-tetrahydro-5H-benz(f)-2,5-oxazocine hydrobromide, m.p. 259°–261° C. The melting point, thin layer chromatographic analysis and infrared spectral analysis all indicate a pure product.

The overall yield of the five steps (beginning with orthobenzoylbenzoic acid) was 60–65 percent of theoretical.

EXAMPLE 2

A mixture of N-(2-hydroxyethyl)-N-methyl-o-benzoylbenzamide (56.66 kg., 200 moles), toluene (10 liters) and phosphorus trichloride (10.07 kg., 10 percent excess) was warmed gently until an exothermic reaction ensued with formation of a hot melt at 77° C. After 0.5 hour at 75° to 77° C., thin layer chromatographic analysis indicated complete formation of the N-(2-chloroethyl)-N-methyl-o-benzoylbenzamide. Isopropanol (90 liters) was quickly added and the batch rapidly cooled, seeded and chilled to below 0° C. Product was collected, washed with cold isopropanol (2×10 liters) and dried to give 50.6 kg. (83.3 percent) of product, m.p. 85.5°–86.2° C.

EXAMPLE 3

A solution of 144 kg. of N-(2-chloroethyl)-N-methyl-o-benzoylbenzamide (481 moles) in 378 kg. of dichloroethane was prepared. A mixture of 50 kg. of this solution, sodium borohydride (273 kg., 721.5 moles, 1.5 equivalents) and dichloroethane (120 liters) at 46° C., was treated with acetic acid (0.5 kg.). The temperature rose steadily to reflux at 86° C. The remaining dichloroethane solution was added slowly, the exotherm maintaining the mixture at reflux without applied heat during the addition and for two hours after addition was complete. Thin layer chromatographic analysis was used to check for the completeness of reaction (had the reaction been found to be incomplete, a small further addition of sodium borohydride could then have been made). The complex was then decomposed by cautious slow addition of 100 liters of water at the reflux temperature and then 50 liters of 40% (w/w) aqueous sodium hydroxide solution to form 2-[N-(2-hydroxyethyl)-N-methylaminomethyl]benzhydrol in dichloroethane. The benzhydrol in dichloroethane was water washed to pH 8 and subsequently cyclized to 5-methyl-1-phenyl-1,3,4,6-tetrahydro5H-benz(f)-2,5-oxazocine as follows:

The organic phase was separated and cooled to 20° C.; 48–50% (224 kg., 149.2 liters) was added with stirring over a half hour period, with cooling to keep the temperature below 50° C. The mixture was gently warmed to reflux, refluxed for 2½ hours, cooled to room temperature and then chilled to 0° C. The product was collected by centrifuging, spun dry, washed with a total of 110 liters acetone and spun dry again. The damp product was returned to a clean vessel previously charged with toluene (242.8 liters), tap water (110.4 liters) and sodium hydroxide pearl (20.4 kg.), and the mixture stirred and heated to 60° C., stirring being continued for ½ hour at 60° C. before standing to separate for ½ hour. The lower aqueous alkaline layer was run off and the toluene layer washed with 2×56 liters of tap water at 60° to 70° C. to pH 7. Toluene was stripped off under reduced pressure and the residual oil cooled to room temperature and then diluted with acetone (220 liters). The solution was clarified by passage via a cartridge filter to a clean vessel. To the stirred, water cooled, clear acetone solution was slowly added hydrochloric acid (38.02 kg., 31.88 liters) over a 178 -1 hour period (to pH 1); the resulting slurry was stirred and cooled to room temperature, then chilled to 0° C. The product was collected by centrifuge, washed well with acetone (total of 110 liters) and sucked dry, and then dried in vacuum oven overnight at 50°–60° C.

Other substituted 2-[N-(2-hydroxyethyl)-N-lower alkylaminomethyl]benzhydrols which can be prepared using the process of the present invention as set forth in the preceding Examples, are shown in Table I.

TABLE I

| Ex. No. | Starting Material | Product |
| --- | --- | --- |
| 4 | 4-methyl-5-methyl substituted o-benzoylbenzamide with NCH₂CH₂OH, CH₃ | corresponding benzhydrol with CH₂NCH₂CH₂OH, CH₃ |
| 5 | 2,4-dichloro substituted o-benzoylbenzamide with C(=O)-N(CH₃)CH₂CH₂OH | corresponding benzhydrol (CHOH) with CH₂NCH₂CH₂OH, CH₃ |

TABLE I-continued
| Ex. No. | Starting Material | Product |
|---|---|---|
| 6 | 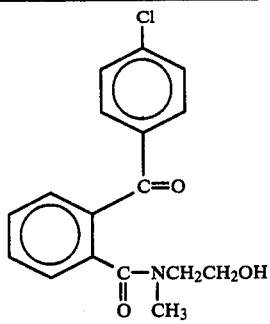 | 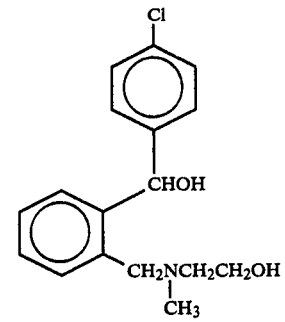 |
| 7 | 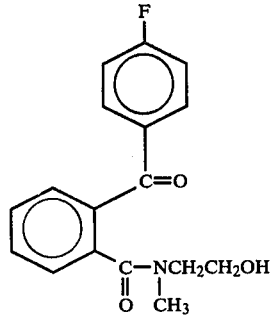 | 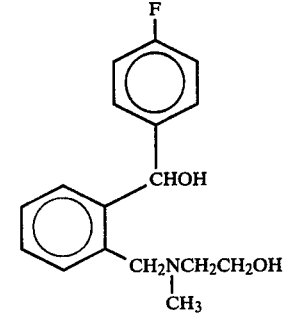 |
| 8 | 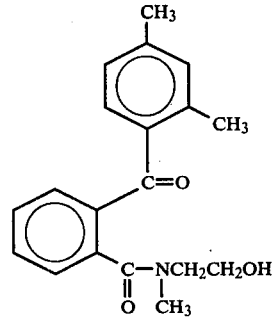 | 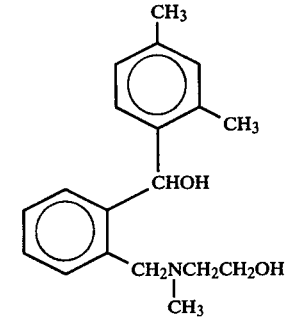 |
| 9 | 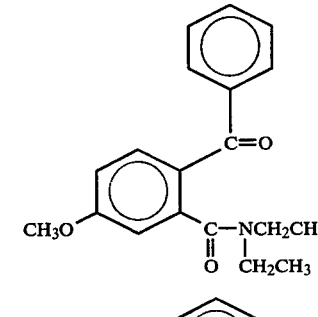 | 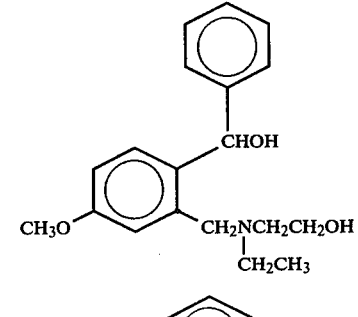 |
| 10 | 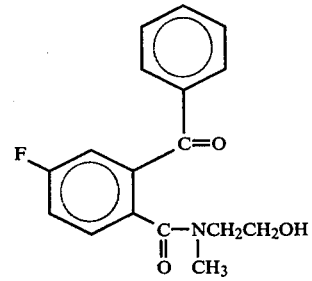 | 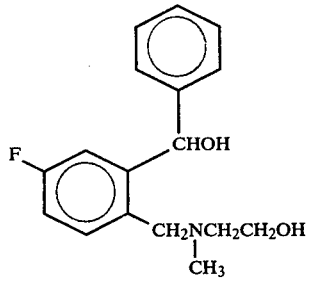 |
What is claimed is:
1. A process for the preparation of 2-[N-(2-hydroxyethyl)-N-lower alkylaminomethyl]benzhydrols of the formula

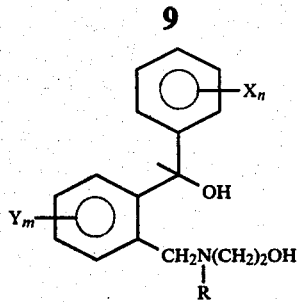

wherein R is methyl or ethyl, X is fluorine, chlorine, bromine or methyl, Y is fluorine, chlorine, methyl or methoxy, and m and n are independently zero, one or two which comprises (1) treating a compound of the formula

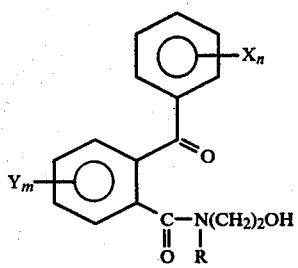

with at least an equimolar amount of a halogenating agent in an inert solvent, to provide a product of the formula

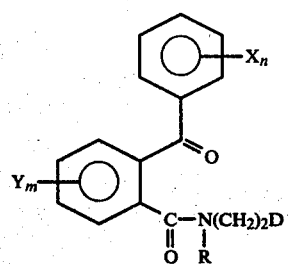

where D is halogen and (2) reducing that product in an inert solvent with sodium borohydride in the presence of an alkanoic acid.

2. A process according to claim 1 wherein D is chlorine.

3. A process according to claim 1 wherein the reduction is conducted by mixing the sodium borohydride with a portion of the alkanoic acid and formula III compound, and thereafter adding the remaining alkanoic acid and formula III compound gradually to the reaction mixture.

4. A process according to claim 1 wherein the alkanoic acid is acetic acid.

5. A process according to claim 1 wherein n and m are zero.

6. A process according to claim 5 wherein the alkanoic acid is acetic acid and D is chlorine.

7. A process for the preparation of 2-[N-(2-hydroxyethyl)-N-lower alkylaminomethyl]benzhydrols of the formula

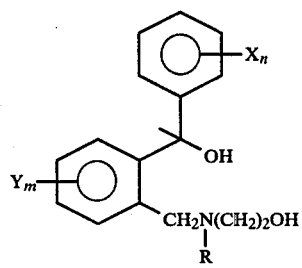

wherein R is methyl or ethyl, x is fluorine, chlorine, bromine or methyl, Y is fluorine, chlorine, methyl or methoxy, and m and n are independently zero, one or two which comprises reducing a compound of the formula

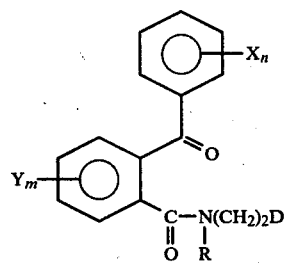

where D is halogen in an inert solvent with sodium borohydride in the presence of an alkanoic acid.

8. A process according to claim 7 wherein D is chlorine.

9. A process according to claim 7 wherein the alkanoic acid is acetic acid.

10. A process according to claim 7 wherein n and m are zero.

11. A process according to claim 10 wherein the alkanoic acid is acetic acid.